(12) United States Patent
Aux Epaules et al.

(10) Patent No.: US 8,956,366 B2
(45) Date of Patent: Feb. 17, 2015

(54) PROSTHETIC ACETABULAR CUP INSERTER AND IMPACTOR

(71) Applicant: Benoist Girard SAS, Herouville-saint-clair Cedex (FR)

(72) Inventors: Arnaud Aux Epaules, Saint Aubin sur Mer (FR); Antoine Coustance, Hérouville St Clair (FR)

(73) Assignee: Benoist Girard SAS (FR)

( * ) Notice: Subject to any disclaimer, the term of this patent is extended or adjusted under 35 U.S.C. 154(b) by 11 days.

(21) Appl. No.: 13/922,709

(22) Filed: Jun. 20, 2013

(65) Prior Publication Data
US 2013/0304072 A1 Nov. 14, 2013

Related U.S. Application Data

(62) Division of application No. 12/991,248, filed as application No. PCT/IB2009/005710 on May 6, 2009, now Pat. No. 8,535,324.

(30) Foreign Application Priority Data

May 7, 2008 (GB) .................................. 0808284.4

(51) Int. Cl.
| | |
|---|---|
| A61B 17/56 | (2006.01) |
| A61B 17/92 | (2006.01) |
| A61B 17/88 | (2006.01) |
| A61F 2/46 | (2006.01) |
| A61F 2/30 | (2006.01) |

(52) U.S. Cl.
CPC ..... *A61F 2/4609* (2013.01); *A61F 2002/30484* (2013.01); *A61F 2002/305* (2013.01); *A61F 2002/4627* (2013.01); *A61F 2220/0025* (2013.01)

USPC .................. 606/91; 606/88; 606/89; 606/99; 606/100

(58) Field of Classification Search
USPC ....................... 606/86 R, 88, 89, 91, 99, 100; 623/22.12
See application file for complete search history.

(56) References Cited

U.S. PATENT DOCUMENTS

| | | | | |
|---|---|---|---|---|
| 5,116,339 | A | * | 5/1992 | Glock ............................. 606/91 |
| 5,683,399 | A | | 11/1997 | Jones |
| 5,954,727 | A | | 9/1999 | Collazo |

(Continued)

FOREIGN PATENT DOCUMENTS

| | | |
|---|---|---|
| EP | 1438936 A1 | 7/2004 |
| EP | 1570815 A1 | 9/2005 |
| EP | 1813229 A1 | 8/2007 |

OTHER PUBLICATIONS

International Search Report, PCT/IB2009/005710, dated Aug. 6, 2009.

*Primary Examiner* — Michael T. Schaper
*Assistant Examiner* — Tracy Kamikawa
(74) *Attorney, Agent, or Firm* — Lerner, David, Littenberg, Krumholz & Mentlik, LLP

(57) ABSTRACT

A prosthetic acetabular cup inserter and impactor has an expandable annular cup engaging element to engage the inner surface of a cup to be inserted in the acetabulum. An expander is provided for expanding the cup engaging element which is connected to one end of a handle via a hollow or partly hollow extension portion. The other end of the handle is provided with an anvil. An elongate operator is located within the extension portion and connected to the cup engaging element. A device is provided for moving the elongate operator to pull the cup engaging element towards the expander.

21 Claims, 3 Drawing Sheets

(56) References Cited

U.S. PATENT DOCUMENTS

| | | | |
|---|---|---|---|
| 7,037,310 B2 * | 5/2006 | Murphy | 606/91 |
| 7,462,180 B2 | 12/2008 | Raugel et al. | |
| 2004/0215200 A1 * | 10/2004 | Tornier et al. | 606/91 |
| 2005/0085915 A1 | 4/2005 | Steinberg | |
| 2007/0225725 A1 * | 9/2007 | Heavener et al. | 606/91 |
| 2008/0058804 A1 * | 3/2008 | Lechot et al. | 606/53 |

* cited by examiner

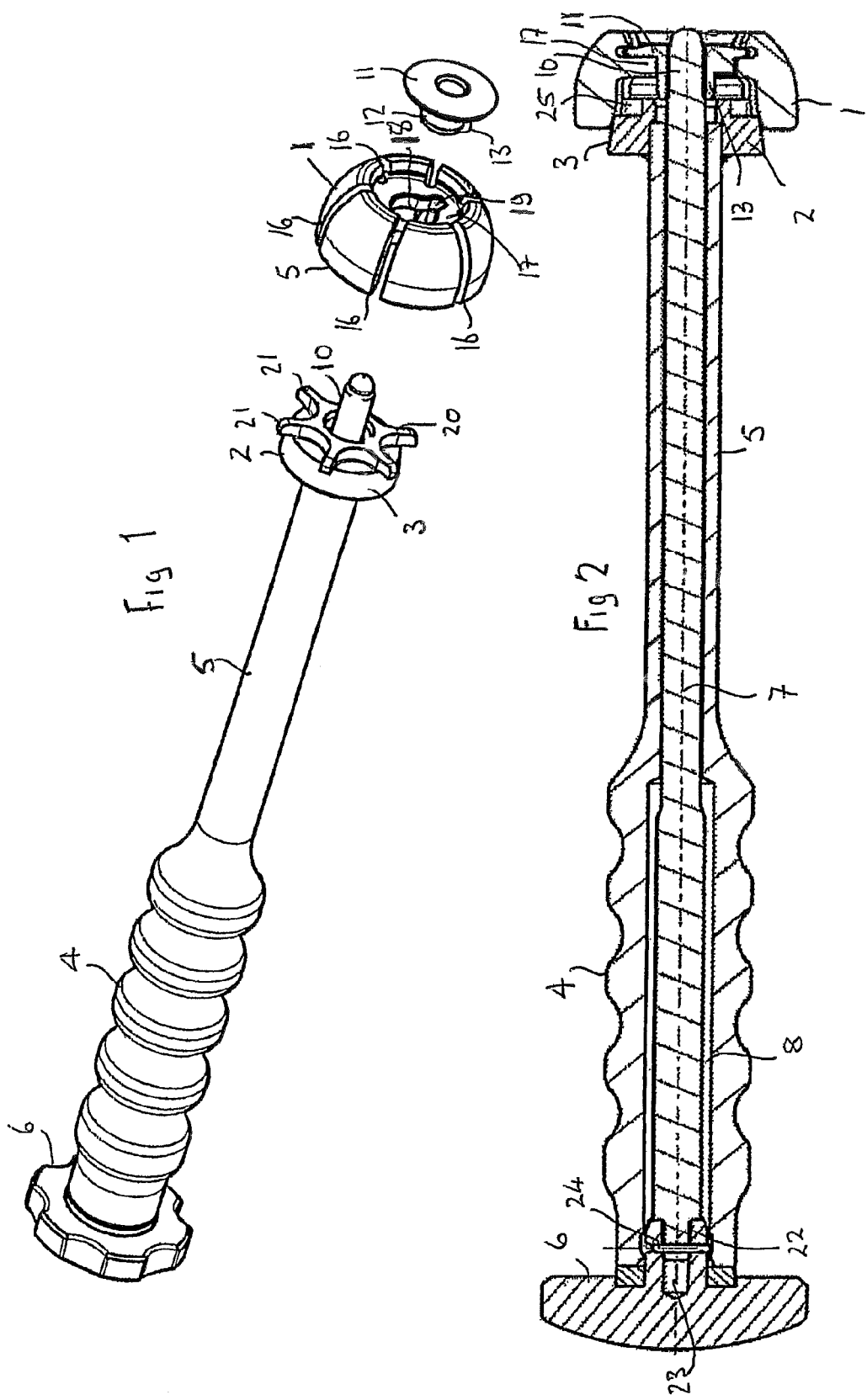

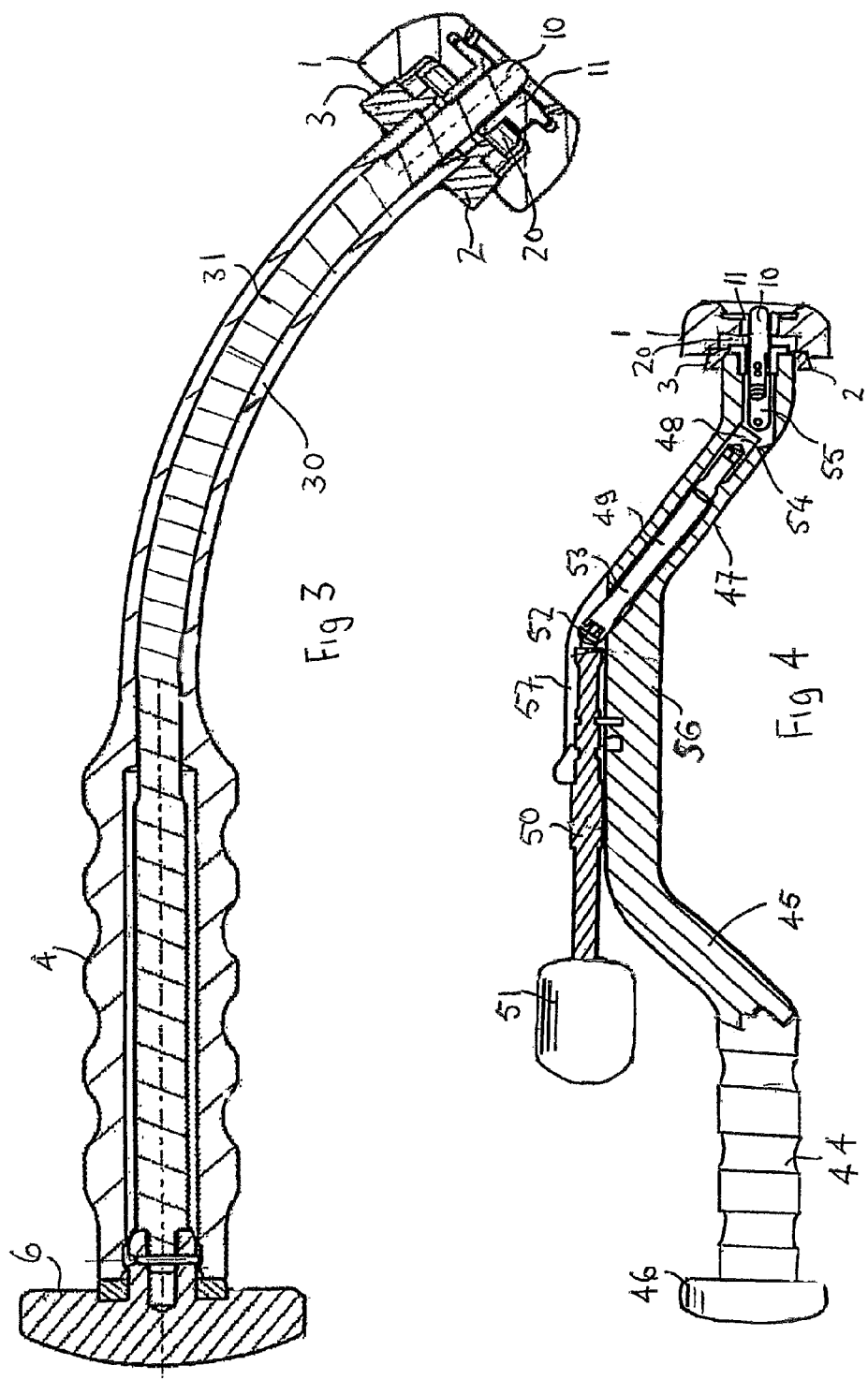

PROSTHETIC ACETABULAR CUP INSERTER AND IMPACTOR

CROSS-REFERENCE TO RELATED APPLICATIONS

The present application is a divisional of U.S. patent application Ser. No. 12/991,248, filed on Nov. 5, 2010 which is a national phase entry under 35 U.S.C. §371 of International Application No. PCT/IB2009/005710, filed May 6, 2009, published in English, which claims the benefit of Great Britain Patent Application No. 08 08284.4, filed May 7, 2008, all of which are incorporated herein by reference.

BACKGROUND OF THE INVENTION

The present invention relates to a prosthetic acetabular cup inserter and impactor.

A prosthetic cup inserter and impactor is shown in U.S. Pat. No. 7,396,357 and U.S. Patent Application Publication No. 2008/0255568, the disclosures of which are incorporated herein by reference which comprises an expandable annular cup engaging element which can be expanded to engage in the inner surface of a cup to be inserted. The structure to expand the engaging element in this construction comprises a screw threaded element which causes relative movement between an extension which carries an expander member and an inner rod which is fastened to the cup engaging element. The relative movement causes the expander to be pressed into the cup engaging element and to cause it to expand. There are a large number of separate parts in this construction which, of necessity, must be disconnected in order to sterilize it.

BRIEF SUMMARY OF THE INVENTION

The present invention is intended to provide an acetabular cup inserter and impactor which includes relatively few parts and which is easily dismantled for sterilization. It also provides an arrangement which can be applied to a straight, curved or cranked construction.

According to the present invention a prosthetic acetabular cup inserter and impactor comprises an expandable annular cup engaging element to engage the inner surface of a cup to be inserted. An expander is provided for expanding the cup engaging element and which is connected to one end of a handle via a hollow or partly hollow extension portion. The other end of the handle is provided with an anvil. An elongate operating element is located within the extension portion and is connected to the cup engaging element. A system is provided for moving the elongate operating element to pull the cup engaging means towards the expander.

Thus, with the present invention an improved operation of the cup expander is provided by pulling the cup engagement element over the expander. Thus, the elongate operating element act in tension when the action to expand the cup engaging element takes place.

It also has the added advantage in that all the apparatus for expanding the cup engaging element can be carried within the cup engaging element itself, the only apparatus outside the cup engaging element being the elongate operating means.

The construction also allows the anvil to be carried so that it acts directly onto the handle and extension portion and into the cup through the cup engaging element rather than through the elongate operating element or other operating apparatus.

Preferably the system for moving the elongate operating element is provided by a screw thread located in the cup engagement element on a co-operating threaded portion of the end of the elongate operating element so that rotation of the elongate operating element causes the cup engagement element to be pulled towards the expander.

The elongate operating element may conveniently comprise a rod, one end of which carries a screw thread to engage a co-operating screw thread located in the cup engagement element and the other end of which is attached to the anvil, and mounted for rotation within the handle of the hollow extension part and which can be rotated by rotating the anvil.

The elongate operating element can have a screw threaded end portion to engagement a threaded retainer located in the cup engaging element.

An anti-rotation device can be provided to prevent the cup engagement element from rotating in relation to the expander, extension portion and handle.

With this arrangement the anti-rotation device may comprise a star wheel attached to the expander and engaging in slots in the cup engagement element.

Preferably the expander is provided by a cone shaped member located on the extension portion and shaped to expand the cup engaging element when they are pulled together.

The extension portion can be curved, bent or cranked along its longitudinal axis and the elongate operating element can therefore include one or more universal joints or be flexible to allow it to rotate in the extension portion.

With this arrangement the elongate operating element can be located in a hollow end portion of the extension portion and projects outwardly therefrom to provide an external portion which can be operated by a separate operating head.

If desired an anti-rotation element can be included for locking the elongate operating element against rotation when in the position in which the cup engaging element is expanded.

BRIEF DESCRIPTION OF THE DRAWINGS

The invention can be performed in various ways and some embodiments will now be described by way of example and with reference to the accompanying drawing in which:

FIG. 1 is a part-exploded isometric view of an acetabular cup inserter and impactor according to the invention;

FIG. 2 is a cross-sectional side elevation of the inserter and impactor shown in FIG. 1;

FIG. 3 is a cross-sectional side elevation of a cup inserter and impactor according to the invention with a curved handle extension;

FIG. 4 is a part cross-sectional side elevation of a cup inserter and impactor according to the invention with a cranked handle extension;

FIG. 5 is a side elevation of the cup engaging end of the insert showing alternative construction; and, FIG. 6 is a cross-sectional side elevation of the construction shown in FIG. 5.

DETAILED DESCRIPTION

As shown in FIGS. 1 and 2 the acetabular cup inserter and impactor according to the present invention comprise an expandable annular cup engaging element 1 to engage the inner surface of a prosthetic cup to be inserted. An expander for expanding the element comprise a cone-shaped member 2 which is in the form of a collar with a tapered outer surface 3. This collar is connected to one end of a handle 4 via a hollow extension portion 5 on which the collar 2 is mounted. The other end of the handle 4 is provided with an anvil 6. An elongate operating element 7 in the form of an operating rod is located within the extension portion 5 and in a bore 8 in the handle 4. One end of the rod 7 is connected to the cup engaging element 1 and means for moving the elongate operating element 7 to pull the cup engaging means 1 towards the expander in the form of the tapered collar 2 are provided by the end of the rod 7 being screw threaded into the expander means 1. The screw threaded portion 10 of the rod 7 engages a screw threaded retainer 11 which has a stem portion 12 on which is provided antirotation lug 13.

The expandable annular cup engaging element 1 is made from a suitable resilient material, for example a resilient synthetic plastics material such as PA (Poly Amide) and comprises a slotted outer rim 15 which, in the example being described, has six slots 16 which extend radially inwardly to a disc-like central portion 17. This central portion 17 has a central opening 18 to receive the stem 12 and a recess 19 to receive the engagement boss 13 on the retainer 11.

The extension 5 also carries a six armed star wheel 20 the arms 21 of which are shaped to engage in the slots 16 in the rim 15 of the cup engaging element 1. The other end of the rod 7 has a reduced portion 22 which is screw threaded into a bore 23 in anvil 6. In order to prevent rotation between the parts they are pinned together by a pin 24, welded or be of monobloc construction.

If the anvil 6 is rotated to screw the end 10 of the rod 7 into the threaded retainer 11 this causes the cup engaging element 1 to be pulled onto the tapered collar 2 and thus cause the cup engaging element to expand outwardly as the cone shaped surfaces 3 enter into a bore 25 in which the star wheel 20 and inner end of the retainer 11 are located.

If the anvil is rotated in the opposite direction the cup engaging element 1 is moved away from the tapered collar 2 and due to its resiliency retracts to a smaller diameter enabling the cup to be released. The star wheel 20 prevents the retainer 11 and the rod from unscrewing when the cup holder is used to orientate the cup along the cup holder's axis.

All the apparatus for expanding the cup engaging element 1 apart from the operating rod 7 is carried within the cup engaging element 1 itself and is on the part of the apparatus which is pulled towards the expander provided by the tapered collar 2.

Impact on the anvil 6 acts directly onto the handle 4 and extension 5 and into the cup to be inserted through the cup engagement element 1 rather than through the elongate rod 7 and its screw threaded operating element to the cup engaging element 1.

The apparatus is simple to dismantle which is achieved merely by unscrewing the anvil 6 and the rod 7 until it frees the retainer 11 leaving only the cup engaging element 1 and retainer 11, the tapered collar 2 and the star wheel 20 being welded to the extension 5 which is in one piece with the handle 4. Thus, there are only four main items for sterilization.

If desired a latch (not shown) can be incorporated to lock the anvil against rotation relative to the handle 4. The device can be made of any suitable material, for example stainless steel, and the anvil 6 of suitably toughened steel to withstand impacts.

FIG. 3 shows a construction with an operating mechanism the same as that shown in FIGS. 1 and 2 but employing a curved handle extension. In this Figure the same reference numerals are used to indicate similar parts to those shown in FIGS. 1 and 2 but in this construction the straight extension portion 5 of FIG. 1 is replaced by a curved extension portion 30 and the straight rod 7 is replaced by an elongate flexible element 31 which can be of any convenient construction but is preferably of the type formed by a wound coil of wire. Such elongate elements can transmit rotary motion. Alternatively the elongate flexible element can be made from a thick wire such as the kind used in heavy bowden cables which are again capable of transmitting rotary motion.

This inserted and impactor can operate in a similar way to that described with regard to FIGS. 1 and 2 and the curved extension is strong enough to carry the impacts on the anvil 6.

FIG. 4 shows another alternative construction in which the same reference numerals are used to indicate the various parts of the operating mechanism in the cup engaging element 1 as in the previous embodiments but in this construction the handle 44 is solid and carries a solid anvil 46. The handle extension portion 45 is cranked and only the outer end 47 is hollow having a longitudinally extending bore 48.

Located in the bore 48 is an elongate operating means in the form of a three-piece rod 49 having one end portion 50 which carries an operating head 51. The length of rod 50 is connected via a universal joint 52 to a centre portion 53 of the rod which is in turn connected by a universal joint 54 to a short straight end portion 55 the outer end of which is threaded in a similar manner to the outer end 10 of the rod 7 in FIGS. 1 and 2 and which engages the retainer 11 in a similar manner.

The end of the extension 45 remote from the handle 44 comprises an end portion which carries the end part 55 of the operating rod so that its axis is substantially co-axial with that of the handle 44.

The upper surface of the central portion 56 of the extension can be provided with a trough 57 in which the end portion 50 of the elongate operating element is located.

With this construction the cup engaging element 1 is expanded and retracted by operation of the head 51. The rotation of the head will cause rotation of elongate operating element through the universal joints and cause the threaded end 10 to pull the cup engaging element towards the tapered collar 2.

Any suitable means of locking can be provided to lock the elongate operating means against rotation relative to the cranked extension 45. The anvil can be used to impact the cup into position.

Figures 5, 6:
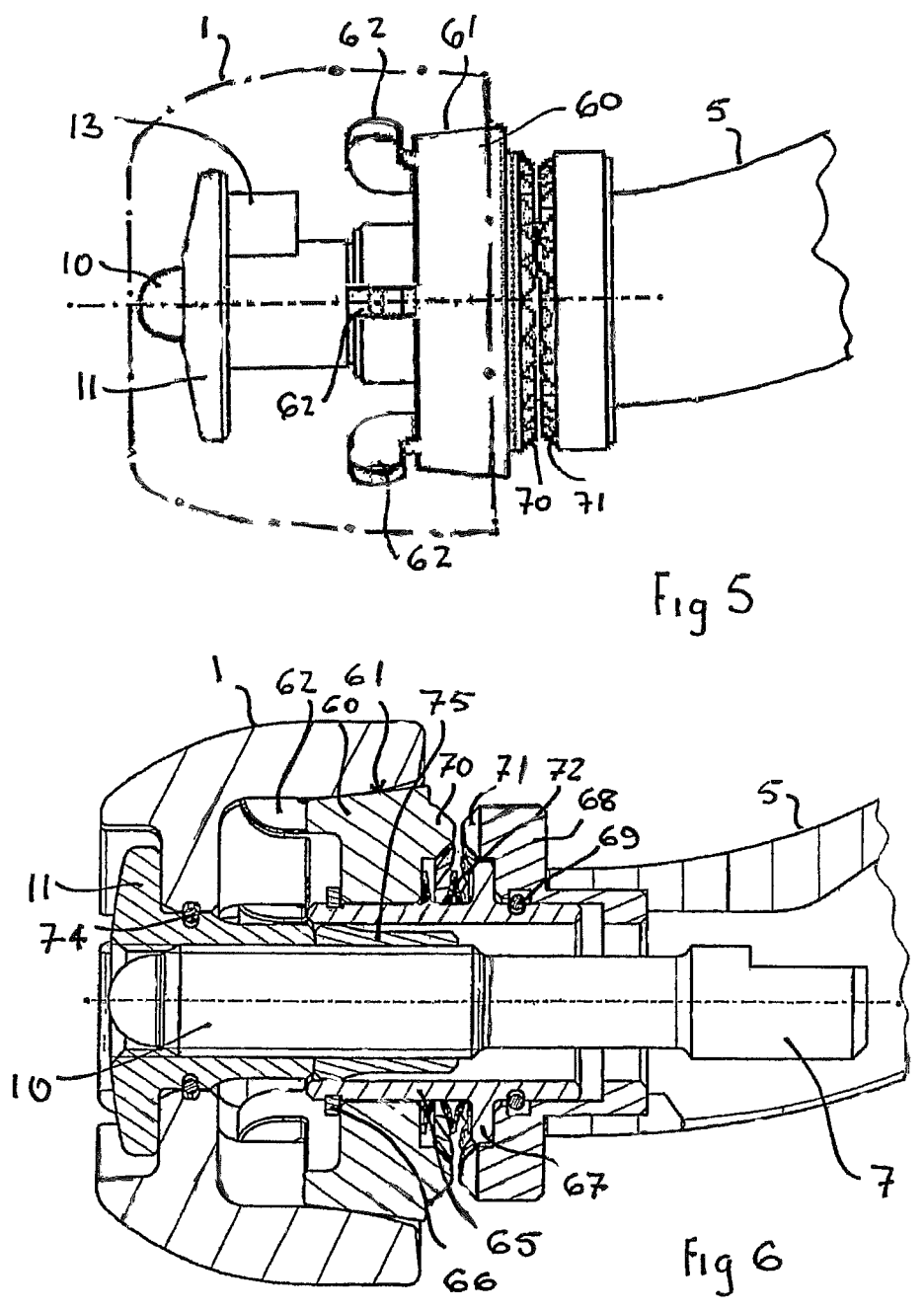

FIGS. 5 and 6 show another alternative construction which provides provision for better cleaning when it is dismantled. In this arrangement the same reference numerals are used to indicate similar parts to those shown in FIGS. 1 to 4 but in FIG. 5 the expandable annular cup engaging element 1 is shown in broken lines so that the construction within it can be seen.

In this construction the cone shaped member 2 and the star wheel 20 of the previous embodiments are replaced by an annular component 60 provided with star-shaped arms 62. The annular component 60 is carried on a sleeve 65 on which it is retained by a circlip 66.

The sleeve 65 has a projecting flange 67 which retains a connection ring 68. A seal 69 is provided between the sleeve 65 and in the connection ring 68 and the ring is rigidly connected to the hollow extension 5. The sleeve 65 is a push fit in the connection ring 68.

The adjacent annular surfaces of the annular member 61 and the retaining ring 68 are provided with co-operating teeth 70 and 71 respectively and a cylindrical compression spring 72 is located on the sleeve 55 between the annular component 60 and the flange 67.

The end 10 of the rod 7 is again screw threaded to receive a retainer 11 of a similar type to that used in the previous embodiments.

A sealing ring 74 is provided between the retainer and the annular cup engaging element 1 which is of similar construction to that shown in the other embodiments. A centralising sleeve 75 is also provided on the screw threaded end 10 of the rod 7 to centralise the rod in the sleeve 65 and to position the annular cup engaging element 1 along the rod 7.

This construction operates in a similar manner that described with regard to the arrangement shown in FIGS. 3 and 4. Thus the star-shaped members 62 engage in the slots 16 and the cone-shaped member provided by the annular component 60 acts to expand the cup engaging element 1.

In the construction shown in FIG. 5 the screw threaded retainer 11 is not quite fully home so that the teeth 70, 71 are not quite in engagement but further movement of the retainer 11 will cause them to engage against the pressure of the compression spring 72. When the parts are to be dismantled the compression spring 72 assists in moving the various parts apart and the annular component 60 is removed from the sleeve 65 by releasing the circlip 66.

With this construction therefore it is possible to assemble the annular cup engaging element 1 onto the expander means provided by the annular member 60 so that the surgeon can place at least part of it in the cup and arrange the angle of the extension 5 to his liking before locking the parts together by further movement of the retainer 11 until the teeth 70, 71 engage.

Once the teeth 70, 71 are engaged, torque can be applied to the cup via extension 5 so that the surgeon can position the cup in the acetabulum to his liking, while maintaining the previously set angle of the extension 5.

The locking mean can be partly released to allow the curved or cranked extension 5 to be rotated in relation to said engaging element 1 without releasing the cup and to be subsequently re-locked when a desired angular position is achieved. Thus, with the cup in position in the acetabulum the surgeon can alter the angle of the extension 5 in relation to the cup by partly releasing the threaded retainer 11 from the annular member 60 to allow the teeth 70, 71 to disengage but for the cup to still be gripped by the engaging element 1, the extension 5 can then be rotated to a different angular position and then re-fastened.

The invention claimed is:

1. A prosthetic acetabular cup inserter and impactor comprising an expandable annular cup engaging element for engaging an inner surface of the prosthetic acetabular cup to be inserted, a handle having a first end, a second end, and a hollow or partly hollow extension portion, a conically tapered expander for expanding the cup engaging element which is connected to the first end of the handle via the hollow or partly hollow extension portion, the second end of the handle provided with an anvil, an elongate operating rod located within the hollow or partly hollow extension portion and connected to the cup engaging element, and a means for moving the elongate operating rod to move the cup engaging element towards the conically tapered expander in which the elongate operating rod has a screw threaded end portion to engage a threaded retainer located in the cup engaging element, in which an anti-rotation element is provided on each of the cup engaging element and the engageable conically tapered expander to prevent the cup engaging element from rotating in relation to the conically tapered expander and wherein the anti-rotation elements comprise an arm attached to the conically tapered expander engaging a slot in the cup engaging element, the conically tapered expander having a first locking element formed thereon, a second locking element connected to the handle for operatively engaging the first locking element, a spring positioned between the first and second locking elements, the elongate operating rod moving the cup engaging element toward the conically tapered expander against a force of the spring to a first position wherein the prosthetic acetabular cup is fixed on the cup engaging element and thereafter to a second position where the first locking element is in engagement with the second locking element to prevent relative rotation between the handle and the conically tapered expander.

2. The prosthetic acetabular cup inserter and impactor as claimed in claim 1 in which the means for moving the elongate operating rod is provided by the threaded retainer located in the cup engaging element in engagement with the screw threaded end portion of the elongate operating rod and the anvil for rotating the elongate operating rod.

3. The prosthetic acetabular cup inserter and impactor as claimed in claim 1 in which the elongate operating rod has a first end which carries the screw threaded end portion to engage the threaded retainer located in the cup engaging element and a second end which is attached to the anvil, and the elongate operating rod is mounted for rotation within said handle and said extension portion, and can be rotated by rotating the anvil.

4. The prosthetic acetabular cup inserter and impactor as claimed in claim 3 wherein the elongate operating rod is locked against rotation with respect to the handle when in the second position in which the cup engaging element is expanded and the first and second locking elements are engaged.

5. The prosthetic acetabular cup inserter and impactor as claimed in claim 4 in which the first and second locking elements can be moved from the second position by the spring force to allow the extension portion to be rotated in relation to the cup engaging element without releasing the cup and to be subsequently re-engaged when a desired angular position is achieved.

6. The prosthetic acetabular cup inserter and impactor as claimed in claim 5 wherein the first and second locking elements each comprise teeth spaced around an annular surface formed on a respective one of the conically tapered expander and the hollow or partly hollow extension portion.

7. The prosthetic acetabular cup inserter and impactor as claimed in claim 1 in which the conically tapered expander has a male conically tapered surface and the cup engaging element is provided with a female conically shaped surface shaped to expand the cup engaging element when the conically tapered expander and the cup engaging element are pulled together.

8. The prosthetic acetabular cup inserter and impactor as claimed in claim 1 in which said cup engaging element and said elongate operating rod can be removed from the handle for cleaning and sterilization.

9. The prosthetic acetabular cup inserter and impactor as claimed in claim 1 in which said extension portion is curved or cranked along a longitudinal axis of the hollow or partly hollow extension portion and the elongate operating rod includes one or more universal joints to allow the elongate operating rod to rotate in the extension portion.

10. The prosthetic acetabular cup inserter and impactor as claimed in claim 1 in which said elongate operating rod is located in a hollow end portion of the hollow or partly hollow extension portion and projects outwardly therefrom to provide an external portion of the elongate operating rod which can be rotated by a separate operating handle.

11. A prosthetic acetabular cup inserter and impactor comprising:
an expandable cup engaging element having a part-spherical outer surface, a central bore, and an end with a conically tapered female opening;
an expander having a central bore and a conically tapered outer surface for engaging the conically tapered female opening of the expandable cup engaging element, the expander including an element engaging the expandable cup engaging element for preventing rotation therebetween;

a handle having a hollow or partially hollow extension portion fixedly coupled to the expander, a hollow portion of the hollow or partially hollow extension portion communicating with the central bore in the expander and the central bore in the expandable cup engaging element;

a rotatable operating rod extending through the hollow or partially hollow extension portion, the central bore in the expander and into the central bore of the expandable cup engaging element, the rotatable operating rod having a threaded end for engaging a threaded element in the central bore of the expandable cup engaging element;

wherein the expander has a first locking element thereon and the handle has a second locking element thereon, a spring element located between the first and second locking elements, the first locking element moveable towards and away from the second locking element upon rotation of the rotatable operating rod, the rotatable operating rod moving the expandable cup engaging element toward the expander against a force of the spring to a first position wherein the prosthetic acetabular cup is fixed on the expandable cup engaging element and thereafter to a second position wherein the first and second locking elements are engaged to prevent relative rotation between the handle and the expander.

12. The prosthetic acetabular cup inserter and impactor as set forth in claim 11 wherein the spring force biases the first and second locking elements away from one another.

13. The prosthetic acetabular cup inserter and impactor as claimed in claim 11 and further comprising an anvil for rotating the rotatable operating rod independently of the handle.

14. The prosthetic acetabular cup inserter and impactor as claimed in claim 13 in which the rotatable operating rod has a first end having the threaded end and a second end attached to the anvil, wherein the rotatable operating rod is mounted for rotation within said handle and said extension portion, and can be rotated by rotating the anvil.

15. The prosthetic acetabular cup inserter and impactor as claimed in claim 14 wherein the rotatable operating rod is locked against rotation with respect to the handle when in the second position in which the cup engaging element is expanded and the first and second locking elements are engaged.

16. The prosthetic acetabular cup inserter and impactor as claimed in claim 15 in which the first and second locking elements can be partly released to allow the extension portion to be rotated in relation to the cup engaging element without releasing the cup and to be subsequently re-engaged when a desired angular position is achieved.

17. The prosthetic acetabular cup inserter and impactor as claimed in claim 16 wherein the first and second locking elements each comprise teeth spaced around an annular surface formed on a respective one of the conically tapered expander and the hollow or partially hollow extension portion.

18. The prosthetic acetabular cup inserter and impactor as claimed in claim 11 in which the conically tapered outer surface of the expander is a male conically tapered surface shaped to engage a surface of the conically tapered female opening of the cup engaging element to expand the cup engaging element when the expander and the cup engaging element are pulled together.

19. The prosthetic acetabular cup inserter and impactor as claimed in claim 11 in which said cup engaging element and rotatable operating rod can be removed from the handle for cleaning and sterilization.

20. The prosthetic acetabular cup inserter and impactor as claimed in claim 11 in which said extension portion is curved or cranked along a longitudinal axis of the hollow or partially hollow extension portion and the rotatable operating rod includes one or more universal joints to allow the rotatable operating rod to rotate in the extension portion.

21. The prosthetic acetabular cup inserter and impactor as claimed in claim 11 in which said rotatable operating rod is located in a hollow end portion of the hollow or partially hollow extension portion and projects outwardly therefrom to provide an external portion of the rotatable operating rod which can be rotated by a separate operating handle.

* * * * *